(12) United States Patent
Manz et al.

(10) Patent No.: US 6,699,378 B2
(45) Date of Patent: Mar. 2, 2004

(54) METHOD FOR CONTROLLING SAMPLE INTRODUCTION IN MICROCOLUMN SEPARATION TECHNIQUES AND SAMPLING DEVICE

(75) Inventors: Andreas Manz, Bettingen (CH); D. Jed Harrison, Edmonton (CA); Carlo S. Effenhauser, Weil am Rhein (DE)

(73) Assignee: Zeptosens AG, Witterswil (CH)

(*) Notice: Subject to any disclaimer, the term of this patent is extended or adjusted under 35 U.S.C. 154(b) by 0 days.

(21) Appl. No.: 09/747,767

(22) Filed: Dec. 22, 2000

(65) Prior Publication Data

US 2001/0023824 A1 Sep. 27, 2001

Related U.S. Application Data

(63) Continuation of application No. 08/226,605, filed on Apr. 12, 1994, now Pat. No. 6,280,589.

(30) Foreign Application Priority Data

Apr. 15, 1993 (DE) .......................................... 93 810 272

(51) Int. Cl.$^7$ ............................................... C25B 15/00
(52) U.S. Cl. ........................ 204/601; 204/603; 204/604
(58) Field of Search ................................ 204/601, 603, 204/604

(56) References Cited

U.S. PATENT DOCUMENTS

| | | |
|---|---|---|
| 4,908,112 A | 3/1990 | Pace |
| 4,941,958 A | 7/1990 | Byers |
| 4,963,498 A | 10/1990 | Hillman et al. |
| 5,144,139 A | 9/1992 | Hillman et al. |
| 5,164,598 A | 11/1992 | Hillman et al. |
| 5,180,480 A | 1/1993 | Manz |
| 5,250,263 A | 10/1993 | Manz |
| 5,288,463 A | 2/1994 | Chemelli |
| 5,296,114 A | 3/1994 | Manz |
| 5,298,134 A | 3/1994 | Zare et al. |
| 5,376,252 A * | 12/1994 | Ekstrom et al. ......... 204/299 R |
| 5,480,614 A | 1/1996 | Kamahori |
| 5,599,432 A | 2/1997 | Manz et al. |
| 5,639,423 A | 6/1997 | Northrup et al. |
| 5,750,015 A | 5/1998 | Soane et al. |
| 5,858,195 A | 1/1999 | Ramsey |
| 6,001,229 A | 12/1999 | Ramsey |
| 6,280,589 B1 | 8/2001 | Manz et al. |
| 6,322,683 B1 * | 11/2001 | Wolk et al. ................. 204/600 |

FOREIGN PATENT DOCUMENTS

| | | |
|---|---|---|
| EP | 356160 A2 | 8/1989 |
| EP | 376611 A2 | 12/1989 |
| GB | 2191110 A | 6/1986 |
| WO | WO91/16966 | 5/1991 |

OTHER PUBLICATIONS

Burggraf, N., et al., "Synchronized Cyclic Capillary Electrophoresis: A Novel Concept for High–Performance Separations Using Low Voltages", *Analytical Methods and Instruments*, 1(1): 55–59 (1993).

Effenhauser, Carlo S., "Effects of Electrokinetic Sample Injection on the Composition of Small Volume Samples in Capillary Electrophoresis", *Analytical Methods and Instrumentation* 1: (3) 172–176 (1993).

Effenhauser, C.S., et al., "Glass Chips for High–Speed Capillary Electrophoresis Separations with Submicrometer Plate Heights", *American Chemical Society* 65: 2637–2642 (1993).

Harrison, D.J., et al., "Miniaturized Chemical Analysis Systems and their Fabrication: An Alternative to Chemical Sensors", *The Electrochemical Society, Inc., Chemical Sensors II*, 93–7: 546–552 (1993).

Harrison, D.J., et al., "Rapid separation of fluorescein derivatives using a micromachined capillary electrophoresis system", *Analytica Chimica Acta*, 283: 361–366 (1993).

Koutny, L.B., et al., "Microscale Chemical Instrumentation: Capillary Separations on a Chip", *Thirty–Third ORN/DOE Conference On Analytical Chemistry in Energy Technology* (1992).

Manz, A., et al., "Design of an Open–tubular Column Liquid Chromatograph Using Silicon Chip Technology", *Sensors and Actuators, B1*: 249–255 (1990).

Manz, A., et al., "Planar Chips Technology for Miniaturization of Separation Systems: A Developing Perspective in Chemical Monitoring", *Advances in Chromatography, 33*: 2–66 (1993).

(List continued on next page.)

*Primary Examiner*—James H. Reamer
(74) *Attorney, Agent, or Firm*—Perkins Coie LLP; Peter J. Dehlinger; Larry W. Thrower

(57) ABSTRACT

In a method for controlling sample introduction in microcolumn separation techniques, more particularly in capillary electrophoresis (CE), where a sample is injected as a sample plug into a sampling device which comprises at least a channel for the electrolyte buffer and a supply and drain channel for the sample. The supply and drain channels discharge into the electrolyte channel at respective supply and drain ports. The distance between the supply port and the drain port geometrically defines a sample volume. The injection of the sample plug into the electrolyte channel is accomplished electrokinetically by applying an electric field across the supply and drain channels for a time at least long enough that the sample component having the lowest electrophoretic mobility is contained within the geometrically defined volume. The supply and drain channels each are inclined to the electrolyte channel. Means are provided for electrokinetically injecting the sample into the sample volume. The resistance to flow of the source and drain channels with respect to the electrolyte buffer is at least about 5% lower than the respective resistance to flow of the electrolyte channel.

3 Claims, 2 Drawing Sheets

OTHER PUBLICATIONS

Pentoney, S.L., et al., "On–Line Connector for Microcolumns: Application to the On–Column *o*—Phthaldialdehyde Derivatization of Amino Acids Separated by Capillary Zone Electrophoresis", *Anal. Chem.*, *60*: 2625–2629 (1988).

Seiler, K., et al., "Planar Glass Chips for Capillary Electrophoresis: Repetitive Sample Injection, Quantitation, and Separation Efficiency", *Anal. Chem.*, *65*: 1481–1488 (1993).

Stegehuis, D.S., et al., "Analyte focusing in capillary electrophoresis using on–line isotachophoresis", *Journal of Chromatography, 591*: 341–349 (1992).

Deml, M., et al., "Electric sample splitter for capillary zone electrophoresis" *Journal of Chromatography 320*:159–165 (1985).

Harrison, D.J., et al., "Capillary Electrophoresis and Sample Injection Systems Integrated on a Planar Glass Chip" *Analytical Chem 64*:(17):1927–1932 (1992).

Harrison, D.J., and Glavina, P.G., "Toward miniaturized electrophoresis and chemical analysis systems on silicon: an alternative to chemical senors" *Sensors and Actuators B10*:107–116 (1993).

Harrison, D.J., et al., "Micromachining a Miniaturized Capillary Electrophoresis–Based Chemical Analysis System on a Chip" *Science 261*:895–897 (1993).

Manz, A., et al., "Miniaturized Total Chemical Analysis Systems: a Novel Concept for Chemical Sensing" *Sensors and Actuators B1*:244–248 (1990).

Verheggen, P.E.M., et al., "Simple sampling device for capillary isotachophoresis and capillary zone electrophoresis" *Journal of Chromatography 452*:615–622 (1988).

\* cited by examiner

METHOD FOR CONTROLLING SAMPLE INTRODUCTION IN MICROCOLUMN SEPARATION TECHNIQUES AND SAMPLING DEVICE

This application is a continuation of application Ser. No. 08/226,605, filed Apr. 12, 1994, now U.S. Pat. No. 6,280,589 which is incorporated herein by reference in its entirety.

The present invention concerns a method for controlling sample introduction in microcolumn separation techniques. The invention also concerns a respective sampling device for a controlled sample introduction in microcolumn separation techniques.

BACKGROUND OF THE INVENTION

Microcolumn separation techniques, in particular capillary electrophoresis has become a very interesting separation technique which is used as part of a sensor or a chemical analysis system. One major reason for this is the great efficiency of the method as a separation technique. The sampling methods usually applied in capillary electrophoresis are: injection of a sample with a syringe, via a septum, in an injection block, the use of injection valves with/without a sample loop, and dipping one end of the capillary tube into the sample reservoir, whereby the sample is introduced by gravity flow, by over- or underpressure, or by electroendosmosis and/or electromigration.

While it is mentioned in Journal of Chromatography, 452, (1988) 612–622, that sample valves are the most suitable sampling method for capillary electrophoresis, there also is described a valveless device for the injection of a sample. The described arrangement comprises a cast capillary block which is connected between an electrode compartment and a sampling device. In the electrode compartment electrolyte solutions contact electrodes. The capillary tube contains measuring electrodes which are connected with an evaluation electronics. The sampling device consists of a broadened part of the capillary tube connected with two feeders which extend perpendicular to the capillary tube. The arrangement of the two feeders off-set from each other along the longitudinal extension of the capillary tube is such, that the sampling device has the shape of a capillary double T structure.

The sample is introduced into the sampling device via a syringe. The injection volume is defined geometrically by the distance which the two feeders are spaced apart along the capillary tube. The transport of the electrolyte solution and the sample in the capillary tube is accomplished by electric fields that are applied between the respective electrodes along the capillary tube. An advantage of the double T shape sampling device, as is also obtained with the use of injection valves, is the concentration effect of dilute sample ionic species. However, it is possible that, allthough no electric field gradient over the feeders exists, sample components from the feeders may diffuse into the capillary tube when the sample has already left the sampling position. The amounts of sample components that uncontrollably enter the capillary tube depend on the diffusion coefficients and the mobilities of the respective sample components. Thus, at the detector there not only arrives a more or less broadened plug of injected sample fluid, depending on the diffusion coefficients and the mobilities of the respective components in the electrolyte and the electric field, but also the electrolyte in front and after or between individual plugs of sample fluid is "polluted" with unpredictable amounts of sample components. These unpredictable amounts of sample components reaching the detector are highly undesirable and result in a high noise of the detected signal, thus reducing the limits of detection considerably.

In Analytical Chemistry, 1992, 64, pages 1926–1932 a capillary electrophoretic device is described in which the sample is injected electrokinetically dipping one end of a capillary into the sample reservoir and applying a voltage across the ends of the capillary. In the electric field the sample is transported electrokinetically and is injected at a T-junction into the channel system of the capillary electrophoretic device. This method, however, leads to a well-known bias of the actual sample composition due to the differences in the electrophoretic mobilities of the sample components. Thus, the sample introduced often does not have the same composition as the original sample. In addition, the volume of the introduced sample is very often unknown such, that internal standards have to be used for quantitative analyses.

SUMMARY OF THE INVENTION

It is therefore an object of the present invention to provide a method for controlling sample introduction in microcolumn separation techniques, and more particularly in capillary electrophoresis (CE), and a sampling device which overcomes the aforementioned disadvantages of the prior art. The sample volume shall be geometrically defined. The composition of the sample which is injected shall not differ from the original composition of the sample in the reservoir. The uncontrolled introduction of sample fluid into the capillary tube shall be reduced considerably. If the unwanted leakage of sample fluid into the capillary tube cannot be totally avoided, provisions shall be made that at least it only occurs in a predictable and controllable manner.

The method and the sampling device according to the invention shall also allow an easy realization of miniaturized analysis concepts, such as the ones described, for example, in Sensors and Actuators B, 10 (1993) 107–116. There the concept of a multi-manifold flow system integrated on a silicon substrate, with valveless switching of solvent flow between channels and electro-kinetic pumping of an aqueous solvent, is described. A similar concept is described, for example, in Analytical Chemistry, Vol.64, No. 17, Sep. 1, 1992, 1926–1932. The described miniaturized chemical analysis system on the basis of capillary electrophoresis comprises a complex manifold of capillary channels, which are micromachined in a planar glass substrate. The transport of the solvent and the sample occurs due to electro-kinetic effects (electro-osmosis and/or electrophoresis).

In order to meet all these and still further objects according to the invention a method for controlling sample introduction in microcolumn separation techniques, in especially in capillary electrophoresis (CE) is provided, wherein an electrolyte buffer and a more or less concentrated sample are transported through a system of capillary channels. The sample is injected as a sample plug into a sampling device which comprises at least a channel for the electrolyte buffer and a supply and drain channel for the sample. The channel for the electrolyte buffer and the supply and drain channels for the sample intersect each other. The supply channel and the drain channel for the sample, each discharge into the channel at respective supply and drain ports. The distance between the supply port and the drain port geometrically defines a sample volume. The supply and the drain channels each are inclined to the electrolyte channel. The injection of the sample plug into the electrolyte channel is accomplished electro-kinetically by applying an electric field across the supply and drain channels for a time at least long enough that the sample component having the lowest electrophoretic mobility is contained within the geometrically defined volume. By this measure the composition of the injected sample plug will reflect the actual sample composition.

In a further preferred process step, immediately after the injection of the sample plug, the electrolyte buffer is allowed to advance into the supply channel and into the drain channel at the respective supply and drain ports for a time period, which amounts to at least the migration time of a slowest component within the sample plug from the supply port to the detector. Thus, the sample is pushed back into the respective supply and drain channels and substantially prevented from uncontrollably diffusing into the electrolyte buffer which is transported past the supply and drain ports. In addition the method allows to control the sample composition within the electrolyte buffer.

The sampling device according to the invention comprises an electrolyte channel, and a supply channel and a drain channel for the sample, which discharge into the electrolyte channel at respective supply and drain ports. The ports are arranged with respect to each other such, that a sample volume is geometrically defined. The supply and drain channels each are inclined to the electrolyte channel. Means are provided for electro-kinetic ally injecting a sample into the sample volume. The resistance to flow of the source and drain channels with respect to the electrolyte buffer is at least about 5% lower than the respective resistance to flow of the electrolyte channel. Preferred variants of the method according to the invention and preferred embodiments of the sampling device according to the invention are subject of the respective dependent claims.

BRIEF DESCRIPTION OF THE DRAWINGS

The invention will become apparent from the following description with reference to the schematic drawings in which.

DETAILED DESCRIPTION OF PREFERRED EMBODIMENTS

Figure 1:
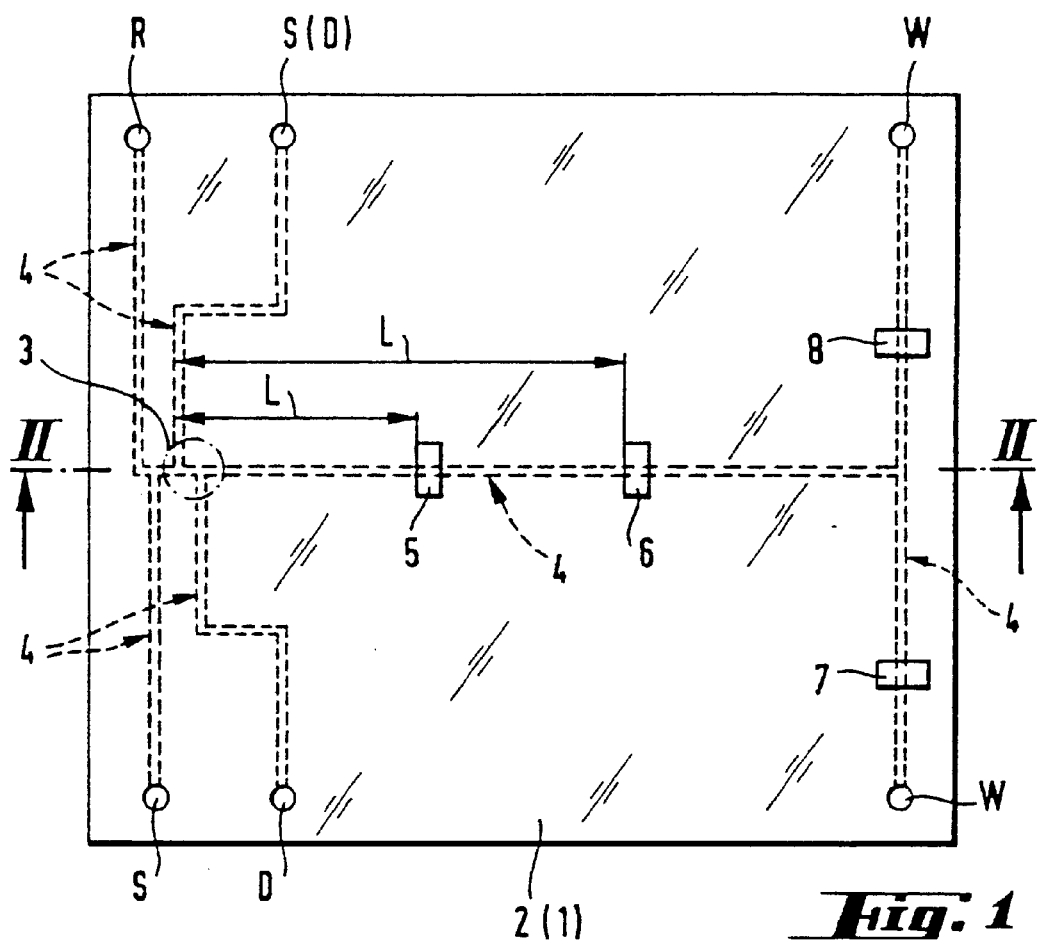
FIG. 1 is a schematic view of a microcolumn separation device which comprises a sampling device according to the present invention.
Figure 2:
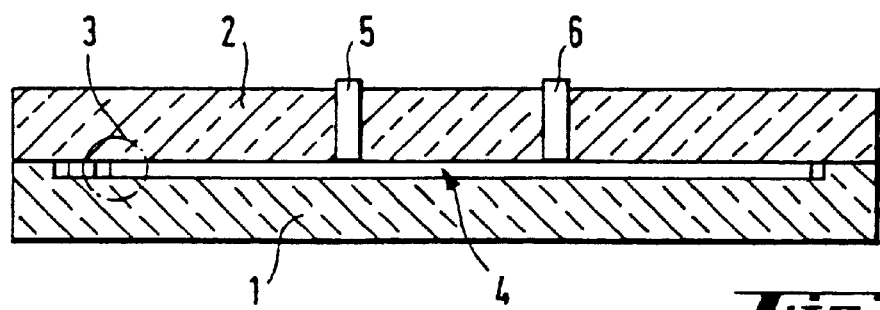
FIG. 2 is a sectional view of the microcolumn separation device according to FIG. 1.

In FIGS. 1 and 2 an exemplary embodiment of a microcolumn separation device, more particularly of an electrophoretic separation device, is depicted. It comprises a base part 1 and a lid part 2. The base part 1 can be made of glass, monocrystalin silicon or other materials known from semiconductor manufacture, or of a suitable polymer material. The lid part 2 is preferably made of glass. The base part 1 comprises a channel system 4 which is etched, micromachined or otherwise established in its surface. Preferably techniques known from semiconductor manufacture are applied for creating the channel system in the surface of the base part 1. The lid part is provided with through holes R, S, D, W, which communicate with the channel system 4 and are adapted to accomodate and hold the ends of capillary tubes. The lid part 2 is also provided with various ports for light waveguides, which are part of an optical detection system, such as, for example, a fluorescence detection system, or an absorption detection system, or a system for the detection of changes of the refractive index of a sample flowing through the channel system. The ports are distributed along the channel system 4 after a sampling device 3, where a sample is introduced into an electrolyte buffer, thus allowing measurements at different locations along the channel system.

The transport of the electrolyte buffer and of the more or less concentrated sample is preferably accomplished by means of electric fields, which are created by switching electric potentials between electrodes of a respective reservoir R and waste receptacles W for the electrolyte buffer and between electrodes associated with respective source S and drain receptacles D for the sample.

Figure 3:
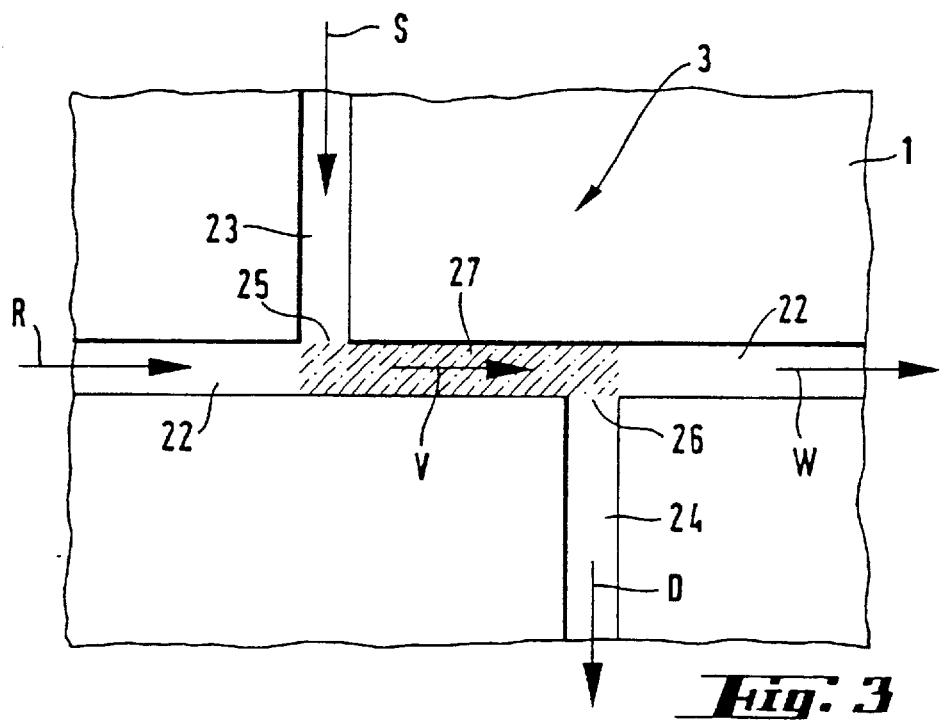
FIG. 3 is an enlarged view of the encircled part of the microcolumn separation device according to FIG. 1, showing a first embodiment of a sampling device.
Figure 4:
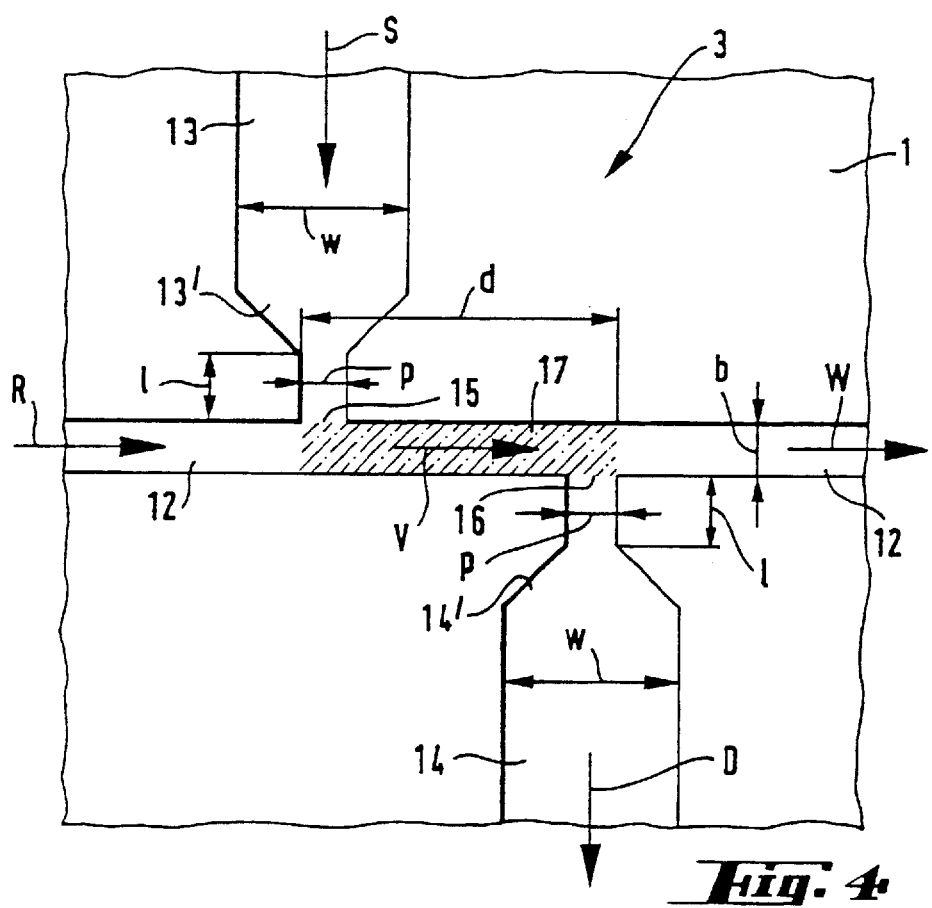
FIG. 4 is a second embodiment of the sampling device.

In FIGS. 3 and 4 the encircled sampling device 3 of FIG. 1 is shown in an enlarged scale. It is part of the flow injection analysis system of FIG. 1, which is based on electro-kinetic principles and allows an electrophoretic analysis of a sample. The sampling device 3 is an integrated part of the capillary channel system 4 and is thus connected with the reservoir R and the waste receptacle W behind the detectors 5–8, for the electrolyte buffer, and with the source receptacle S and the drain receptacle D for the sample which is to be analyzed. In FIGS. 3 and 4, for the sake of clarity the reservoir R and the receptacles W, S, D are not drawn, but they are only symbolized by arrows, which at the same time indicate the direction of fluid flow in the channel system 4.

In FIG. 3 a first exemplary embodiment of the sampling device is shown. It comprises a capillary channel piece 22, which on one end is connected to a capillary channel communicating with the reservoir R for the electrolyte buffer and in longitudinal direction on the other end with a capillary channel where the electrophoretic separation of the sample takes place, and which leads to the detector(s) and in further consequence to the waste receptacle(s) W. The sampling device further comprises a supply channel 23, which communicates with a source receptacle S for the sample, and a drain channel 24 which leads to a drain receptacle D. The source channel 23 and the drain channel 24 are inclined to the longitudinal extension of the channel piece 2, preferably they are arranged about perpendicular such, that together with the channel piece 22 they form a double T structure, as shown in the drawing. The source channel S and the drain channel D each discharge into the channel piece 22 at respective supply and drain ports 25, 26. According to the drawing in FIG. 3 the supply port 25 and the drain port 26 are spaced apart from each other longitudinally at the channel piece 22 such, that a sample volume 27 is geometrically defined as will be explained in more detail hereinafter. It is to be understood, that the drain channel 24 can be arranged in direct longitudinal extension of the source channel 23 such, that the supply and drain ports 25, 26 are situated opposite each other. In that case the channels of the sampling device have no double T structure, but they are arranged in form of an ordinary crossing.

As already mentioned before the transport of the fluids, i.e. the electrolyte buffer and the sample, is accomplished with electric fields, which are a result of different electric potentials at the reservoir R and the waste receptacle W for the electrolyte buffer, and the respective source receptacle S and the drain receptacle D for the sample. By applying, for example, a positive electric potential to the reservoir R and a negative electric potential to the waste receptacle, the electrolyte buffer is electro-kinetically transported from the reservoir R through the capillary channel system to the waste receptacle W. In order to introduce the sample into the channel piece 22, for example, the source receptacle S for the sample is maintained at a positive potential and the drain receptacle D is kept on a negative potential. In the resulting electric field the sample is transported electro-kinetically from the source receptacle S to the drain receptacle D. The direction of flow is indicated in FIG. 3 by the arrows S, V, and D. By this measure, a part 27 of the channel piece 22, which is delimited by the supply port 25 on the one end and by the drain port 26 on the other end is filled with sample. Thus, the sample-filled part 27 of the channel piece of the sampling device 3 defines the volume of the electro-kinetically injected sample plug, which is indicated by the hatchings in FIG. 3. In other words, the volume 27 of the sample plug is geometrically delimited by the spaced apart supply and drain ports 25 and 26. In the aforementioned case that the supply and drain ports are arranged opposite each other, such that the channel piece 22 and the supply and drain channels 23, 24 form an ordinary crossing, the size and volume of the intersection determines the sample volume. Thus, in that case, the sample volume is only defined by the cross-sections of the respective channels 22, 23, 24.

In order to assure that the composition of the sample in the sample volume 27 reflects the actual sample composition in the reservoir R the electric field across the supply and drain channels 23, 24 must be maintained for at least for a time period long enough that the geometrically defined sample volume is filled and contains the the component of the sample which has the lowest electrophoretic mobility. This minimum time period $t_{min}$ is given by the equation $t_{min}=d/\mu_i \cdot E$. In this equation d stands for the distance, which the source and drain port are spaced apart; $\mu_i$ is the total mobility of the slowest component i of the sample, which will be referred to in more detail hereinafter, E is the field strength across the source and drain channels, which results from the difference in potentials.

When a electrophoretic analysis of a sample is to be carried out, first an electric field between the reservoir R and the waste receptacle W is established such, that the electrolyte buffer is transported from the reservoir R to the waste receptacle W. After the channel system of the chemical analysis system has been filled with the electrolyte buffer, the injection of the sample into the channel piece 22 is initiated. For that purpose an electric field is established between the source receptacle S and the drain receptacle D such, that the sample is electro-kinetically transported from the source receptacle S through the supply channel 23 via the channel piece 22 into the drain channel 24 and on to the drain receptacle D. It is understood that during the time period, in which the sample is injected, the electric field between the reservoir R and the waste receptacle W is switched off, or that the potentials are chosen such, that the sample only is transported along the path described above. After the injection time period which is chosen such, that it is ensured that the sample volume 27 between the supply port 25 and the drain port 26 is filled with the sample, the electric field between the source receptacle S and the drain receptacle D is switched off. At the same time the electric field between the reservoir R and the waste receptacle W is activated again such, that the sample contained within the sample volume 27 is transported on into the direction of the detector(s) and the waste reservoir. While it is transported through the channel system the sample is separated electrophoretically in the electric field.

The problem of leakage or diffusion of sample components into the electrolyte buffer while it is transported past the supply and drain ports 23 and 24, even though no electric field is applied between the source receptacle S and the drain receptacle D, is solved by allowing the electrolyte buffer to advance into the supply channel 23 and into the drain channel 24 at the respective supply and drain ports 25 and 26 for a time period, which amounts to at least the migration time $t_i$ of the slowest component i within the sample plug from the supply port 25 to the respective detector. Thus, the sample is pushed back into the supply and drain channels 23, 24 and substantially prevented from uncontrollably diffusing into the electrolyte buffer which is transported past the supply and drain ports 25, 26.

The migration time $t_i$ of the slowest component i of the sample is defined as the quotient between the separation length L and the product of the total mobility $\mu_i$ of the slowest component i of the sample and the electric field strength E' acting on it along its path L, and is given by the equation $T_i=L/(\mu_i \cdot E')$. In this equation the separation length L (FIG. 1) is the distance the sample component i travels between the supply port 25 and the respective activated detector 5–8, and the total mobility $\mu_i$ of the component is the sum of the electrophoretic mobility $\mu_{i,ep}$ of the component and the overall electro-osmotic mobility $\mu_{eo}$ of the sample. The time period during which the detection is accomplished is very short in comparison to the migration time of the slowest component of the sample and thus is neglectable.

In order to allow the electrolyte buffer to advance into the supply and drain channels 23 and 24, in the exemplary embodiment of the sampling device depicted in FIG. 3 the source receptacle S and the drain receptacle D are switched on an electric potential which is different from the electric potential at the reservoir R for the electrolyte buffer, thus establishing a potential difference of suitable magnitude. In an embodiment, where the electrolyte buffer is transported from a positive potential to a negative potential, the potentials at the source and drain receptacles S, D are chosen negative with respect to the positive potential at the reservoir R. In case of a transport of the electrolyte buffer from a negative potential to a positive potential the potentials of the source and drain receptacles S, D are chosen positive with respect to the reservoir R.

Preferably the potential difference between the reservoir R and the source and drain receptacles S, D is chosen such, that the resultant electric field has a field strength which amounts to at least about 0.1 V/cm.

Another approach to allow an advancement of the electrolyte buffer into the supply and drain channels 3, 4 is depicted in FIG. 4. The construction of the depicted sampling device 3 basically corresponds to the one depicted in FIG. 3. It comprises a channel piece 12 with two side channels 13, 14. The side channels are inclined to the longitudinal extension of the channel piece 12 an angle that amounts to from about 5 degrees to about 175 degrees; however, preferably they are arranged about perpendicular with respect to the channel piece 12. The side channels are a supply channel 13 and a drain channel 14, which discharge into the channel piece 12 at respective supply and drain ports 15, 16. Preferably the supply port 15 and the drain port 16 are spaced apart from each other at the channel piece 12 and delimit a sample volume 17. The distance d which they are spaced apart from each other typically amounts to from about 0 μm to about 3 cm, most preferably to about 3 mm, wherein the value 0 indicates that the supply and drain ports are located opposite each other. The channel piece 12 communicates with a reservoir R and a waste receptacle W for the electrolyte buffer. The supply channel 13 is connected with a source receptacle S for the sample, while the drain channel 14 communicates with a drain receptacle D.

The sampling device 3 is part of an electrophoretic chemical anlysis system and basically functions in the same way as the sampling device depicted in FIG. 3. However, in order to allow the electrolyte buffer to advance into the supply and drain channels 13, 14 the resistance of flow within the two channels is reduced. In particular the source channel and the drain channel each have a resistance to flow with respect to said electrolyte buffer, which is about 5% lower than the respective resistance to flow of said electrolyte channel. Surprisingly the reduction of the resistance to flow of the supply and drain channels 13, 14 does not result in an increase of the leakage or diffusion of sample components into the electrolyte buffer as it is transported past the respective supply and drain port 15, 16. Instead, the reduction of the resistance to flow of the side channels 13, 14 leads to a convective flow of the electrolyte buffer into the channels 13, 14, even when the aplied electric fields should not result in such a flow. Thus, the leakage or diffusion of sample components is considerably decreased and the noise of the detected signal is reduced. In consequence the sensitivity of the analytic system, that is the limit of detection, is increased. The resistance to flow of the supply and drain channel can be deminished by either reducing the length of the respective channels or by increasing their respective widths w. Preferably the reduction of the resistance to flow of the supply and drain channels 13, 14 is achieved by providing them each with a width w that is at least about two times greater than the width p of the supply and drain ports 15, 16. Such, the supply and drain channels 13, 14 each have about the shape of a bottle, the bottle neck being the respective supply or drain port 15, 16.

While it is possible that the supply and drain channels 13, 14 empty directly into the channel piece 12 such, that their ends, which are located right next to the channels piece 12 are the respective source and drain ports 15, 16, from where the width of the channels gradually increases over a respective intermediate piece 13', 14' from the width p of the ports to the final width w of the channels, the supply and drain ports also have longitudinal extensions l. Thes longitudinal extensions correspond at least to the width p of the respective supply and drain ports 15, 16. It is advantageous, if the widths p of the supply and drain port 15, 16 are kept constant along their longitudinal extension l. In a preferred embodiment the widths p of the supply and drain port 15, 16 are chosen such, that they about correspond to the width b of the channel piece 12.

The depth of the channel piece 12 (which should correspond to the depth of the channel system that it is part of) and of the supply and drain channels 13, 14 typically amounts to from about 0.1 $\mu$m to about 100 $\mu$m. The depths of the bottle-neck-like supply and drain port 15, 16 about corresponds to the depth of the channels.

The sampling device 3 according to the invention has been explained with reference to exemplary embodiments which are part of micro-analysis chips. It can as well be an arrangement of capillary tubes, which is part of a electrophoretic chemical analysis system made of capillary tubes. In the most preferred embodiment, however, the sampling device is integrated into a system of capillary channels which are established in a small planar sheet of glass, semiconductor material, or a suitable polymer. Advantageously the channel system including the supply and drain channels and the respective supply and drain ports are etched or micromachined or casted (in case of a polymer base part), or otherwise established in the planar substrate. Most suitable for its manufacture are techniques which are well established in semiconductor production or in the manufacture of micromechanical elements.

The combination of a structure that geometrically defines the injected sample volume with an electro-kinetic injection of the sample over a defined minimum time period allows to relyably control the sample volume and to assure that the composition of the sample contained within the sample volume reflects the original composition of the sample in the reservoir. A further improvement of the method and the sampling device according to the invention allows a considerable reduction of uncontrolled leakage or diffusion of sample components into the electrolyte buffer. Thus, it is possible to reduce the leakage or diffusion such, that the still occuring leakage results in a concentration of the sample in the electrolyte buffer, that is less than 3% of the original concentration of the sample. By this measure the noise of the detected electrophoretic signal is reduced and the detection limits are increased.

What is claimed is:

1. A microfluidics device comprising a substrate having an upper surface, a channel network formed in the substrate, including a source channel adapted to contain a sample, a drain channel, and an electrolyte channel adapted to contain an electrolyte buffer, wherein said source and drain channels are each inclined with respect to the electrolyte channel, and which source and drain channels intersect said electrolyte channel at a source port and a drain port, respectively, wherein movement of sample material from the source to the drain channel is effective to place a sample volume between the source and drain ports in the electrolyte channel, a lid attached to the substrate's upper surface, enclosing the channels in the substrate, and openings in the lid communicating with the channel network and adapted to hold capillary tubes therein, for introducing liquid from the tubes into associated channels in the device.

2. The device of claim 1, wherein said channels terminate at and are in fluid communication with reservoirs, and said openings are aligned to communicate with said reservoirs.

3. The device of claim 1, wherein said source and drain ports are offset along the length of said electrolyte channel, forming an elongate sample volume within said electrolyte channel, between and including said ports.

* * * * *